United States Patent [19]

Zou et al.

[11] Patent Number: 5,677,162
[45] Date of Patent: Oct. 14, 1997

[54] METHOD FOR ACTIVATING PROTHROMBIN TO THROMBIN

[75] Inventors: Jinsheng Zou, Bronx, N.Y.; John Hamman, Baltimore, Md.; Gerard Marx, New York; Bernard Horowitz, New Rochelle, both of N.Y.

[73] Assignee: New York Blood Center, Inc., New York, N.Y.

[21] Appl. No.: 432,955

[22] Filed: May 1, 1995

[51] Int. Cl.$^6$ .................. C12N 9/74; C12N 7/04; C12N 7/06; A61K 38/48
[52] U.S. Cl. .................. 435/214; 435/236; 435/238; 424/94.64
[58] Field of Search .................. 435/214, 236, 435/238; 424/94.1, 94.64

[56] References Cited

U.S. PATENT DOCUMENTS

| | | | |
|---|---|---|---|
| 4,160,025 | 7/1979 | Eibl et al. | 424/101 |
| 4,965,203 | 10/1990 | Silbering et al. | 435/188 |
| 5,143,838 | 9/1992 | Kraus et al. | 435/214 |
| 5,151,355 | 9/1992 | Crawley et al. | 435/214 |
| 5,219,995 | 6/1993 | Herring et al. | 530/381 |
| 5,260,420 | 11/1993 | Burnouf-Radosevich et al. | 530/382 |
| 5,304,372 | 4/1994 | Michalski et al. | 424/94.64 |
| 5,354,682 | 10/1994 | Kingdon et al. | 435/214 |
| 5,393,666 | 2/1995 | Linnau | 435/183 |
| 5,397,704 | 3/1995 | Boctor et al. | 435/214 |

OTHER PUBLICATIONS

"Activation of Human Prothrombin by Human Prothrombinase" by Krishnaswamy et al. date Mar. 5, 1987, vol. 262, No. 7, pp. 3291–3299 in The Journal of Biological Chemistry.

"Hydrophobic Affinity Chromatography of Human Thrombin" by Lundblad et al. dated Apr. 1993–vol. 302, No. 1, pp. 109–112 in Archives of Biochemistry and Biophysics.

"Characterization of a Stable From of Human Meizothrombin Derived form Recombinant Prothrombin" dated Apr. 15, 1994, vol. 269, No. 15, pp. 11374–11380 in The Journal of Biological Chemistry. H.C.F. Cote et al.

"Human Thrombins" by Fenton et al. dated Jun. 10, 1977, vol. 252, No. 11, pp. 3587–3598 in The Journal of Biological Chemistry.

"Initiation of the Extrinsic Pathway of Blood Coagulation: Evidence for the Tissue Factor Dependent Autoactivation of Human Coagulation Factor VII" by Nakagaki et al. dated Nov. 12, 1991, vol. 30, No. 45 in Biochemistry.

"Tissue Factor Potentiates the Factor VIIa–catalyzed Hydrolysis of an Ester Substrate" by Higashi, et al., dated Sep. 5, 1992, vol. 267, No. 25, pp. 17990–17996 in The Journal of Biological Chemistry.

"Importance of Factor Xa in Determining the Procoagulant Activity of Whole–blood Clots" by Eisenberg et al. dated May 1993, vol. 91, pp. 1877–1883 in Journal of Clinical Investigation.

"Intrinsic Prothrombin Activation" by Rosemary Biggs. In *Human Blood Coagulation* Chapter 5, pp. 66–80.

37 Snake Venoms Affecting the Haemostatic Mechanisms—A Consideration of their Mechanisms, practical applications and biological significance, by N.A. Marsh dated 1994, vol. 5, pp. 399–410 in Blood Coagulation and Fibrinolysis.

*Primary Examiner*—Michael G. Wityshyn
*Assistant Examiner*—Kristin K. Larson
*Attorney, Agent, or Firm*—Amster, Rothstein & Ebenstein

[57] ABSTRACT

The present invention provides a method for activating prothrombin to thrombin in a prothrombin complex composition comprising at least prothrombin, Factors V, VII, IX, and X, and phospholipid, comprising the steps of: (a) cold-incubating the prothrombin complex composition with 2–15 mM of $Ca^{2+}$ ions at a pH of 6.5–8.0 and at a temperature of 2°–8° C. until Factor VII contained in the composition is activated; and (b) incubating the cold-incubated composition at a pH of 6.5–8.0 and at a temperature of 10°–25° C. for a period of time sufficient to activate prothrombin contained in the composition to thrombin.

34 Claims, 4 Drawing Sheets

METHOD FOR ACTIVATING PROTHROMBIN TO THROMBIN

BACKGROUND OF THE INVENTION

Thrombin (Factor IIa) is a proteolytic enzyme derived from prothrombin (Factor II). It converts fibrinogen to fibrin monomers, which form insoluble polymers and are cross-linked by the action of Factor XIII. Thrombin has been used in combination with fibrinogen as a fibrin glue or a fibrin sealant. Thrombin also is an activator of Factors V, VII, IX, XIII and Protein C, and therefore has been used as a separate hemostasis product.

Prothrombin conversion to thrombin is accomplished by the action of prothrombinase complex which contains phospholipids, Factors Va and Xa, and calcium ions. During the purification of prothrombin, however, some of the clotting initiation factors which lead to the formation of Factors Va and Xa, such as Factors XI, XII, and tissue factor are separated from prothrombin. Once prothrombin is isolated from these clotting initiation factors, prothrombin activation proceeds very slowly.

Most commercial methods used today for activating thrombin therefore rely upon the addition of exogenous activators such as snake venoms and thromboplastin from rabbit brain or other animal sources to initiate activation. Such animal-activated thrombin preparations, however, have the potential to cause adverse side effects if the exogenous activator is not completely removed from the thrombin preparation.

Accordingly, there exists a need to activate prothrombin without using these exogenous animal components. The present invention satisfies this need by providing a method for activating prothrombin to thrombin without the addition of exogenous animal activators by controlling various conditions such as pH, temperature, and calcium concentration.

SUMMARY OF THE INVENTION

It is therefore an object of the present invention to provide a method for activating prothrombin to thrombin in a prothrombin complex composition comprising at least prothrombin, Factors V, VII, IX, and X, and phospholipid, comprising the steps of:

(a) cold-incubating said prothrombin complex composition with 2–15 mM of $Ca^{2+}$ ions at a pH of 6.5–8.0 and at a temperature of 2°–8° C. until Factor VII contained in said composition is activated; and (b) incubating said cold-incubated composition at a pH of 6.5–8.0 and at a temperature of 10°–25° C. for a period of time sufficient to activate prothrombin contained in said composition to thrombin.

It also is an object of the present invention to provide a method for preparing a thrombin concentrate from a prothrombin complex composition comprising at least prothrombin, Factors V, VII, IX, and X, and phospholipid, comprising the steps of:

(a) cold-incubating said prothrombin complex composition with 2–15 mM of $Ca^{2+}$ ions at a pH of 6.5–8.0 and at a temperature of 2°–8° C. until Factor VII contained in said composition is activated;

(b) incubating said cold-incubated composition at a pH of 6.5–8.0 and at a temperature of 10°–25° C. for a period of time sufficient to activate prothrombin contained in said composition to thrombin; and (c) subjecting the composition containing thrombin to ion exchange chromatography to obtain the pure thrombin concentrate.

Additional objects of the invention will be apparent from the description which follows.

DETAILED DESCRIPTION OF THE INVENTION

Figure 1:
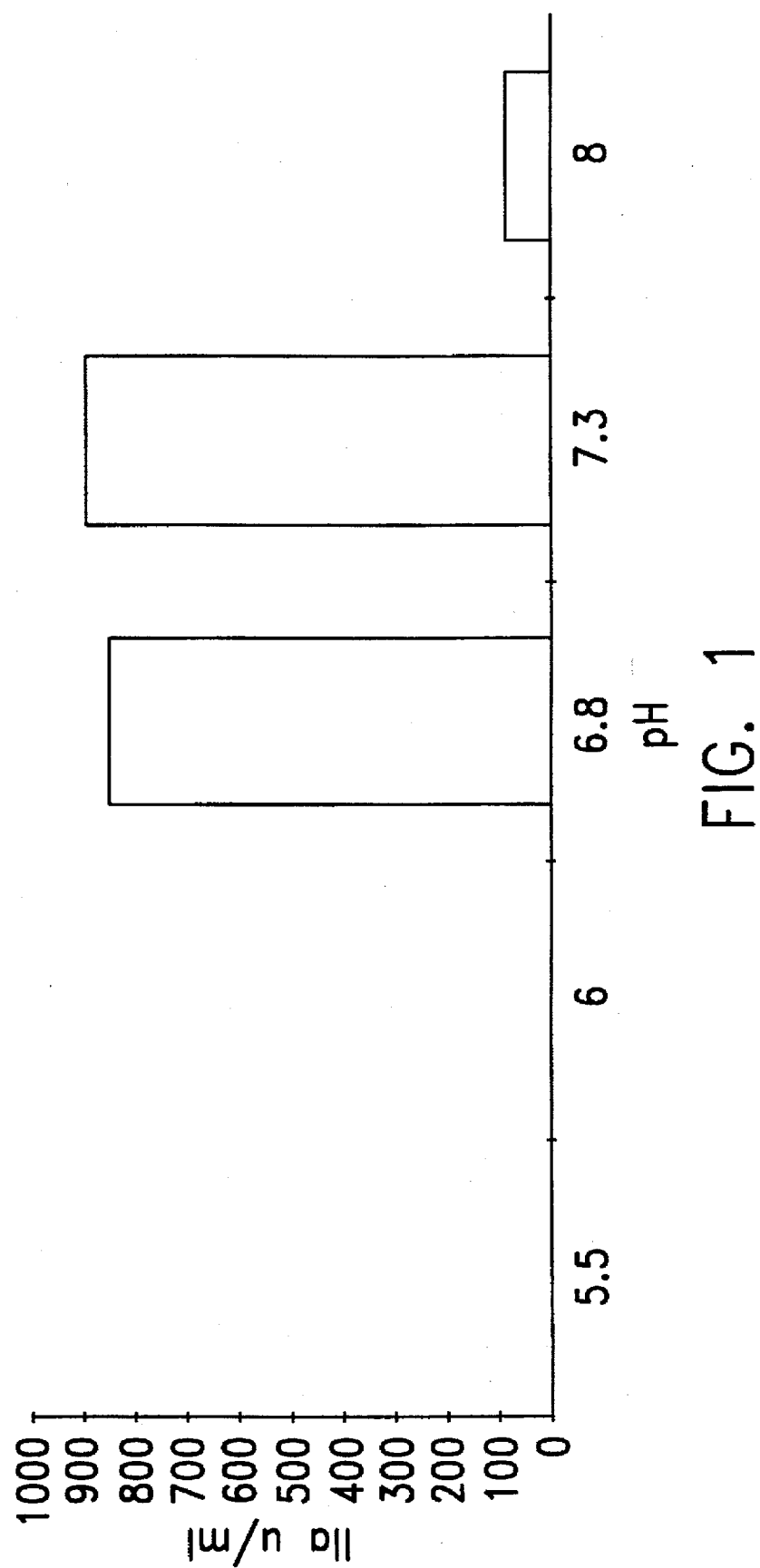
FIG. 1 represents the effect of pH on activation of prothrombin.

The present invention provides a method for activating prothrombin to thrombin in a prothrombin complex composition. As used herein, "prothrombin complex composition" is defined as a partially purified composition from human blood which comprises at least prothrombin, Factors V, VII, IX, and X, and phospholipid.

The prothrombin complex composition may be isolated from plasma fractions known in the art such as Cohn Fraction III and PPSB, preferably Cohn Fraction III. Additional sources for the prothrombin complex composition will be readily apparent to one skilled in the art, and include recombinantly produced prothrombin material.

Cohn Fraction III may be prepared from plasma by using the classical Cohn-Oncley cold ethanol procedures (Cohn, E. J, et al. *J. Am. Chem. Soc.* 68:459–475 (1949); Oncley, J. L., et al.. *J. Am. Chem. Soc.* 71:541–550 (1949)). Likewise, PPSB may be prepared as described in Chandra, S., Brummelhuis, H. G. J. *Vox Sang* 41:257–273 (1981). Alternatively, Cohn Fraction III (and its precursor fraction, Fraction II+III) may be obtained commercially from the American National Red Cross, Bethesda, Md., Armour Pharmaceutical Co., Kankakee, Ill. and other sources.

The prothrombin complex composition may be isolated from Cohn Fraction III as follows. Fresh or frozen Fraction III paste (1:1.875 w/w) is suspended in Buffer A (4% polyethylene glycol 8000, 100 mM sodium chloride, 20 mM tris [hydroxymethyl] aminomethane, pH 7.0) at room temperature for 1 hour with stirring. After 1 hour additional Buffer A is added (8,125 kg/kg Fraction III, w/w) and the temperature of the mixture is lowered to 3°±1° C. The solution is stirred for 1 hour, and then transferred to 1 L polypropylene centrifuge bottles and stored overnight at 3°±1° C. The precipitate is removed by centrifugation at 3500 rpm in a cooled (3°±3° C.) batch type centrifuge (Beckman J6B) for 20 minutes. The supernatant is then collected and the precipitate is discarded. The supernatant is warmed to room temperature (20°±3° C.) and the pH is adjusted to 7.00±0.05 with 0.5M sodium hydroxide or 0.5M hydrochloric acid. The pH adjusted supernatant is then clarified by filtering through a 0.45 micron filter (Sartorius, SARTOBRAN pH filter, or equivalent) which had been washed with WFI or Buffer A at a quantity of 4 kg/ft².

The filtrate is then pumped onto a DEAE FRACTOGEL, M650 (85 gm/kg filtrate) chromatography column equilibrated with Buffer B (125 mM sodium chloride, 20 mM tris [hydroxymethyl] aminomethane), pH 7.0. The DEAE column is then washed with Buffer B, and the prothrombin complex composition is eluted from the column with Buffer C (500 mM sodium chloride, 20 mM tris [hydroxymethyl] aminomethane, pH 7.0).

To activate the prothrombin, the prothrombin complex composition is first incubated with 2–15 mM $Ca^{2+}$ ions from a source such as $CaCl_2$ at a pH of 6.5–8.0 and at a temperature of 2°–8° C., until Factor VII contained in said composition is activated. In the preferred embodiment, the calcium concentration is 3–10 mM, and most preferably 4–6 mM, the pH is preferably 6.8–7.3, and most preferably 6.8–7.1, and the temperature is preferably 3°–6° C. The optimal calcium concentration, pH, and temperature may vary and will depend upon the total concentration of prothrombin, Factors V, VII, IX, and X, and phospholipid present in the starting prothrombin complex composition, as well as their respective ratios. Preferably, the total concentration is at least 3–10 mg/ml. The cold incubation should be performed for a sufficient time to permit activation of all or substantially all (about 90% or greater) of the Factor VII contained in the prothrombin complex composition. The optimal time may be determined by measuring Factor VIIa activity (or concentration) at various stages of the cold incubation using Quick's one-stage clotting assay with Factor VIIa deficient plasma (Sigma Diagnostics), and plotting the results on a graph. All or substantially all of the Factor VII will be activated when the Factor VIIa activity (or concentration) reaches a maximum value. A subsequent decrease in the Factor VIIa activity (or concentration) may indicate that the Factor VIIa has undergone degradation. At a total protein concentration of 3–10 mg/ml, all or substantially all of the Factor VII will be activated in at least 8 hours, and preferably 12–18 hours.

In the second step of the method, the cold-incubated composition is then incubated at a pH of 6.5–8.0 and at a temperature of 10°–25° C., for a period of time sufficient to activate prothrombin contained in said composition to thrombin. In the preferred embodiment, the pH is preferably 6.8–7.3, and most preferably 6.8–7.1, and the temperature is preferably 18°–23° C. The pH and temperature may vary and will depend upon the total concentration of prothrombin, Factors V, VII, IX, and X, and phospholipid present in the starting prothrombin complex composition.

The optimal time for activation of prothrombin to thrombin may be determined by measuring thrombin activity (or concentration) at various stages of the incubation by the conversion of fibrinogen into fibrin (R. L. Lundblad *Biochemistry* 10:2501–2506 (1971), or by the activation of a chromogenetic substrate (CHROMOZYM TH, Boehringer), and plotting the results on a graph. All or substantially all of the prothrombin will be activated when the thrombin activity (or concentration) reaches a maximum value. It is preferred that the incubation be stopped at the earliest signs of a decrease in thrombin activity (or concentration) to prevent degradation of thrombin.

At a total protein concentration of 3–10 mg/ml, the activation of thrombin should occur at about 48–120 hours, and preferably at about 72 hours. However, the time required for activation of prothrombin to thrombin will depend upon the concentrations of prothrombin, Factors V, VII, IX, and X, and phospholipid in the prothrombin complex composition. At higher concentrations of some or all of these components, the time for activation will proceed faster.

The present invention also provides a method for preparing a thrombin concentrate from a prothrombin complex composition. That method comprises performing the two incubation steps above, and further comprises subjecting the composition containing thrombin to ion exchange chromatography to obtain the thrombin concentrate. The ion exchange chromatography may comprise one or more runs with different columns. The choice of columns, buffers and pH will be evident to those skilled in the art. In addition to ion exchange chromatography, the purification also may comprise an additional purification step using affinity chromatography.

In the particularly preferred embodiment, the ion exchange chromatography comprises subjecting the composition containing thrombin from the incubation steps to two different columns: a DEAE column followed by an SP-SEPHAROSE column. The chromatography on these columns is preferably performed as follows.

The composition containing thrombin is first applied to a DEAE column (Tosohaas, TOYOPEARL 650M or equivalent) equilibrated with an equilibration buffer containing 20 mM tris [hydroxymethyl] aminomethane and 125 mM sodium chloride, pH 7.0, and the resulting material passed through the column is collected. The column is then rinsed with a rinse buffer containing 20 mM tris [hydroxymethyl] aminomethane and 125 mM sodium chloride, pH 7.0, and the resulting material passed through the column is again collected, and combined with the first collection. The unactivated prothrombin and most other proteins bind to the column while the thrombin (activated prothrombin) passes through the column.

The combined resulting eluates are then applied to an SP-SEPHAROSE column (Pharmacia, or equivalent; 400 gm SP-SEPHAROSE per liter of pH adjusted DEAE pass-through pool) equilibrated with an equilibration buffer containing 20 mM tris [hydroxymethyl] aminomethane and 125 mM sodium chloride, pH 8.0. The column is then rinsed with a rinse buffer containing 20 mM tris [hydroxymethyl] aminomethane and 150 mM sodium chloride, pH 8.0. The thrombin concentrate is eluted with an elution buffer containing 20 mM tris [hydroxymethyl] aminomethane and 300 mM sodium chloride, pH 8.0.

The present invention also provides subjecting the composition containing thrombin to at least one viral inactivation treatment. The viral inactivation treatment is preferably conducted on the composition containing thrombin prior to ion exchange chromatography, and may include inactivation treatments known in the art such as solvent-detergent and/or UV light treatments. In the particularly preferred embodiment, the composition containing thrombin is subjected to both solvent-detergent and UV light treatments. The solvent-detergent is also preferably tri-n-butyl phosphate and TWEEN 80.

It also is within the confines of the present invention that the thrombin concentrate may be subjected to filtration with a 15 nm filter (Asahi PLANOVA 15 N, Japan, or equivalent). It is believed that the use of this filter will remove at least 5.5 log10 of HAV, EMC, Parvo B19, VSV, Sindbis, and possibly other viral particles which may be contained therein. This filtration is preferably performed following the ion exchange chromatography step.

The ion exchange chromatography purified thrombin concentrate may then be adjusted to 20–200 NIH equivalent thrombin units/ml with the addition of up to 15 mM calcium chloride, up to 1.0% polyethylene glycol 4600, up to 300 mM sodium chloride, and up to 40 mM tris [hydroxymethyl] aminomethane. The formation is then filtered through a sterile 0.2 micron filter (Sartorius SARTOBRAN pH, or equivalent) into a sterile container.

The present invention is described in the following examples which are set forth to aid in an understanding of the invention, and should not be construed to limit in any way the invention as defined in the claims which follow thereafter.

EXAMPLE 1

Isolation of Prothrombin Complex Composition

Fresh or frozen Fraction III paste (1:1.875 w/w) was suspended in Buffer A (4% polyethylene glycol 8000, 100 mM sodium chloride, 20 mM tris [hydroxymethyl] aminomethane, pH 7.0) at room temperature for 1 hour with stirring. After 1 hour additional Buffer A was added (8.125 kg/kg Fraction III, w/w) and the temperature of the mixture was lowered to 3°±1° C. The solution was stirred for 1 hour, and then transferred to 1 L polypropylene centrifuge bottles and stored overnight at 3°±1° C. The precipitate was removed by centrifugation at 3500 rpm in a cooled (3°±3° C.) batch type centrifuge (Beckman J6B) for 20 minutes. The supernatant was collected and the precipitate discarded. The supernatant was then warmed to room temperature (23°±3° C.) and the pH was adjusted to 7.00±0.05 with 0.5 sodium hydroxide. The pH adjusted supernatant was then clarified by filtering through 0.45 micron filter (Sartorius, SARTOBRAN pH filter) which had been washed with Buffer A at a quantity of 4 kg/ft$^2$.

DEAE FRACTOGEL, M650 (850 gm/kg filtrate) was equilibrated in a chromatography column with Buffer B (125 mM sodium chloride, 20 mM tris [hydroxymethyl] aminomethane), pH 7.0. The filtrate was then pumped onto the DEAE column and the column was subsequently washed with Buffer B. The prothrombin complex composition was eluted from the column with Buffer C (500 mM sodium chloride, 20 mM tris [hydroxymethyl] aminomethane, pH 7.0). The column out flow was monitored with a UV absorbance detector and the UV absorbance peak (OD 280) was collected.

EXAMPLE 2

Effect of pH on Activation of Prothrombin

The prothrombin complex composition isolated as described in Example 1 was separated into five different samples and 0.5M sodium hydroxide or 0.5M hydrochloric acid was added to each sample to adjust the pH of samples 1–5 to 5.5, 6, 6.8, 7.3 and 8, respectively. The activation of the prothrombin in each sample was allowed to proceed at 22° C. for 5 days. After 5 days, the amount of thrombin in each sample was determined by thrombin clotting assay. The results are presented in FIG. 1. The effect of various pH levels on the amount of thrombin was as follows: at pH 5.5,<1.1 u/ml; at pH 6.0, 5 u/ml; at pH 6.8, 874 NIH u/ml; at pH 7.3, 906 u/ml; and at pH 8, 83 u/ml.

EXAMPLE 3

Effect of Ca$^{2+}$ Concentration on Activation of Prothrombin

Figure 2:
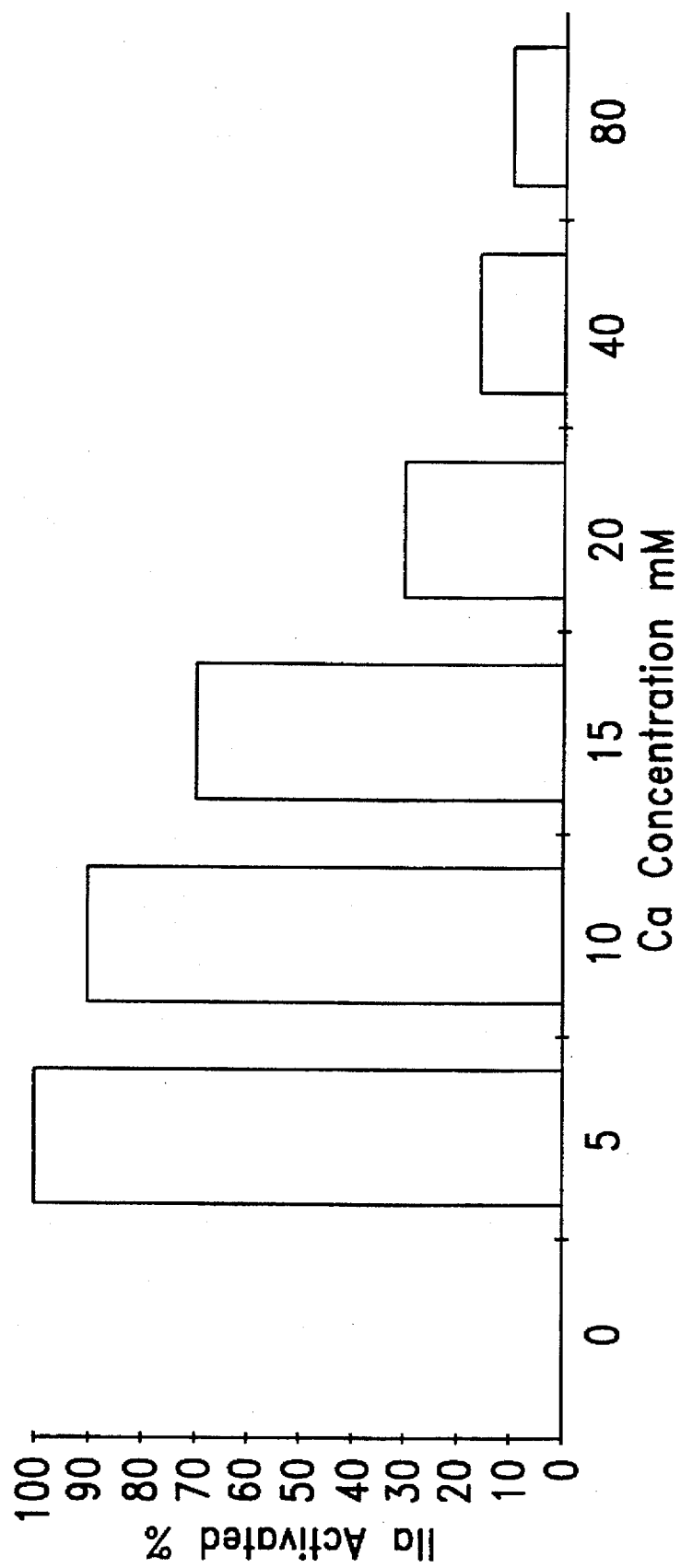
FIG. 2 represents the effect of calcium concentration on activation of prothrombin.

The prothrombin complex composition isolated as described in Example 1 was separated into seven different samples and CaCl$_2$ was added to samples 1–7 to a final concentration of 0, 5, 10, 15, 20, 40, and 80 mM, respectively. The activation of the prothrombin contained in each sample was allowed to proceed at 22° C. for 3 days. The concentration of both activated thrombin and nonactivated prothrombin in each sample was then determined by thrombin clotting assay. The results are presented in FIG. 2. The effect of CaCl$_2$ concentration on the percent of prothrombin activated was as follows: at 0 mM, 0%; at 5 mM, 100%; at 10 mM, 89%; at 15 mM, 70%; at 20 mM, 30%; at 40 mM, 16%; and at 80 mM, 11%.

EXAMPLE 4

Effect of Cold Pre-Incubation on Activation of Prothrombin

Figure 3:
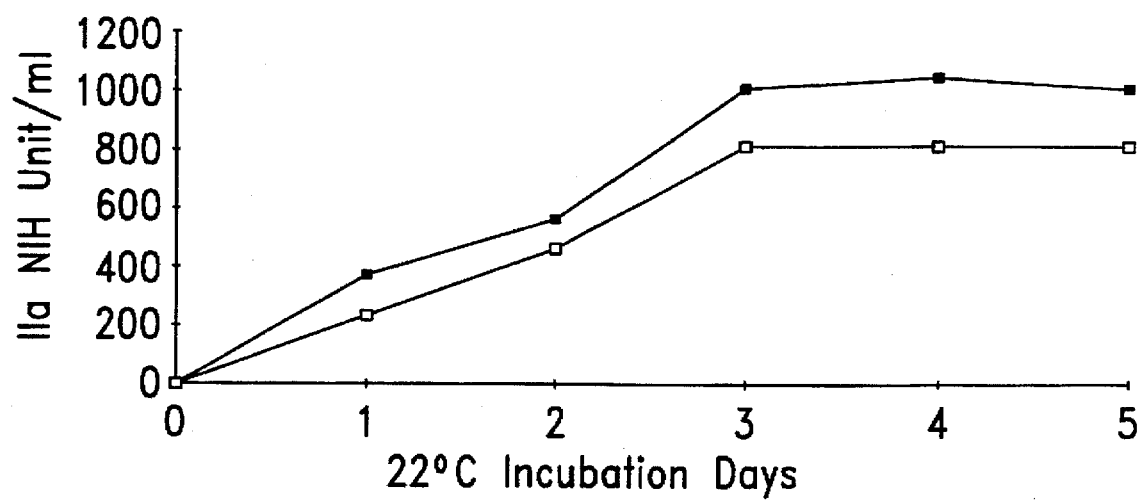
FIG. 3 represents the effect of cold pre-incubation on activation of prothrombin.

The prothrombin complex composition isolated as described in Example 1 was separated into twelve different samples. 5 mM CaCl$_2$ was added to six samples at a pH of 7.0, and the samples were incubated at 4° C. for 8–12 hours. Following preincubation of the first six samples at 4° C., 5 mM CaCl$_2$ was added to the remaining six samples at a pH of 7. All samples were then incubated at 22° C. for 5 days. The activity of thrombin was then measured at days 0, 1, 2, 3, 4, and 5 for each sample using thrombin clotting assay. The results are presented in FIG. 3. The effect of pre-incubation at 4° C. on thrombin activity in the first six samples at days 0–5 (FIG. 3, ■) was as follows: at day 0, 0 NIH Units/ml; at day 1, 344 NIH Units/ml; at day 2, 542 NIH Units/ml; at day 3, 987 NIH Units/ml; at day 4, 1013 NIH Units/ml; and at day 5, 975 NIH Units/ml. The corresponding activities of thrombin contained in the samples not preincubated at 4° C. (FIG. 3, □) was as follows: at day 0, 0 NIH. Units/ml; at day 1, 210 NIH Units/ml; at day 2, 433 NIH Units/ml; at day 3, 788 NIH Units/ml; at day 4, 784 NIH Units/ml; and at day 5, 763 NIH Units/ml.

EXAMPLE 5

Effect of Time and Temperature on Activation of Prothrombin

Figure 4:
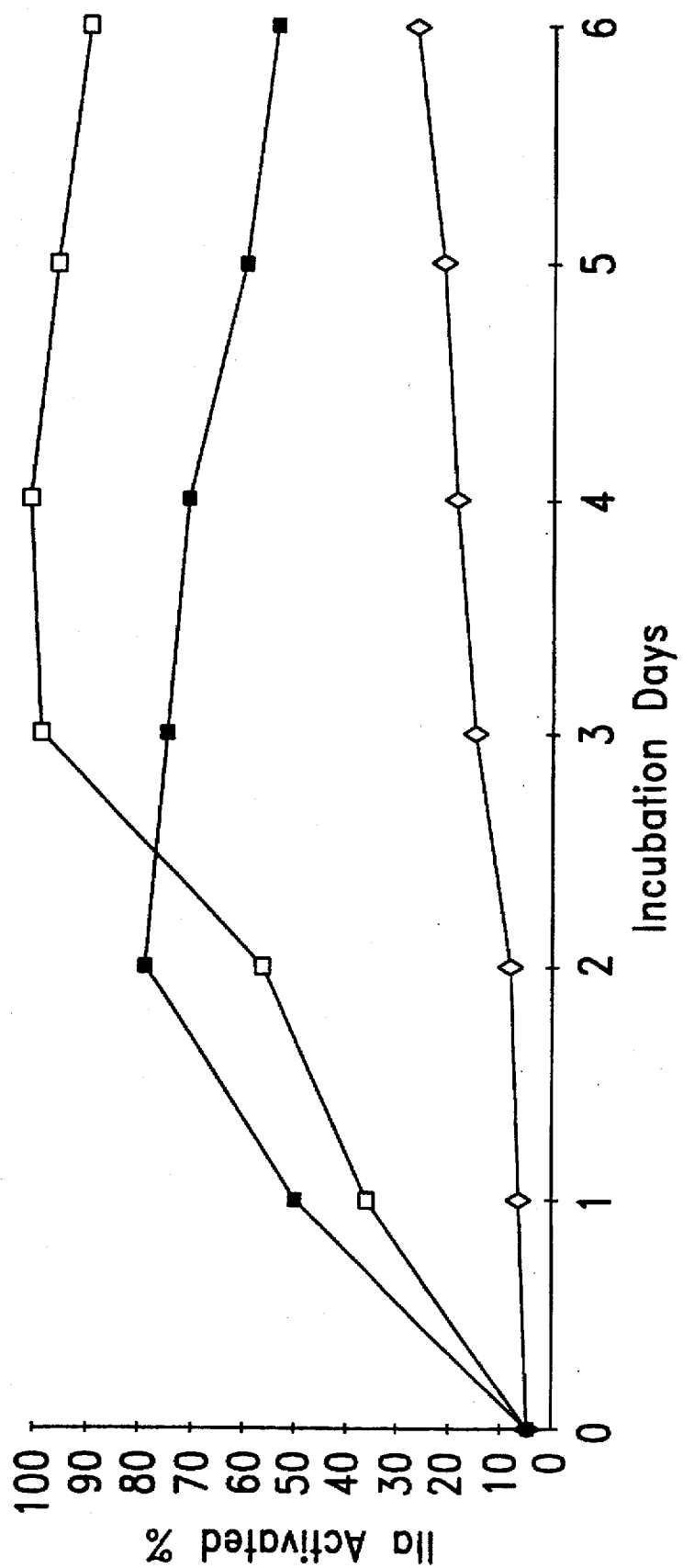
FIG. 4 represents the effect of time and temperature on activation of prothrombin.

The prothrombin complex composition isolated as described in Example 1 was separated into three different samples. 5 mM CaCl$_2$ was added to each sample at a pH of 7, and the three samples were incubated at 4° C., 22° C., and 37° C., respectively, for six days. The activity of thrombin contained in each sample was measured at days 0, 1, 2, 3, 4, 5, and 6 using thrombin clotting assay. The results are presented in FIG. 4. The thrombin activity in the sample incubated at 4° C. at days 0–6 (FIG. 4, ◊) was as follows: at day 0, 5 NIH Units/ml; at day 1, 6.5 NIH Units/ml; at day 2, 8 NIH Units/ml; at day 3, 15 NIH Units/ml; at day 4, 19 NIH Units/ml; at day 5, 22 NIH Units/ml; and at day 6, 28 NIH Units/ml. The thrombin activity in the sample incubated at 22° C. at days 0–6 (FIG. 4, □) was as follows: at day 0, 5 NIH Units/ml; at day 1, 35 NIH Units/ml; at day 2, 55 NIH Units/ml; at day 3, 97 NIH Units/ml; at day 4, 99 NIH Units/ml; at day 5, 95 NIH Units/ml; and at day 6, 89 NIH Units/ml. The thrombin activity in the sample incubated at 37° C. at days 0–6 (FIG 4, ■) was as follows: at day 0, 5 NIH Units/ml; at day 1, 49 NIH Units/ml; at day 2, 78 NIH Units/ml; at day 3, 75 NIH Units/ml; at day 4, 71 NIH Units/ml; at day 5, 59 NIH Units/ml; and at day 6, 53 NIH Units/ml.

EXAMPLE 6

Preferred Method for Activation of Prothrombin Composition 5 mM CaCl$_2$ was added to the prothrombin complex composition isolated as described in Example 1 at a pH of 6.9–7.1. The solution was cooled to 5°±3° C. and stirred for about 12–18 hours at 5°±3° C. The solution was then warmed to room temperature (18°–23° C.), and incubated for 72 hours at that temperature. Following incubation the solution was filtered through a 0.45 (Sartorius, SARTOBRAN pH filter) and 0.2 micron filters (Millipore ACTRO 50) which were washed with Buffer B at a quantity of 4 kg/ft$^2$. The pH was then adjusted to 7.00±1 with 0.5M sodium hydroxide.

EXAMPLE 7

UV Virus Inactivation

The thrombin containing composition was then subjected to UV virus inactivation by pumping it through a UVC irradiator with average UV dosage of 0.206 J/cm$^2$. A quencher, such as Rutin, was added to thrombin at a concentration of 0.1mM to 0.5 mM. Thrombin composition contained 3–10 mg/ml protein, and an activity of 1000–2000 NIH U/ml. After treatment, the thrombin activity was measured by clotting assay. UVC treatment killed all enveloped viruses and nonenveloped viruses, e.g. HAV, VSV, Sindbis, and Parvo B19 at over 5.5 logs, while thrombin activity was maintained at 70–80%.

EXAMPLE 8

Solvent Detergent Virus Inactivation

Tri-n-butyl phosphate (TnBP) and 20% TWEEN 80 was added to the pH adjusted activated prothrombin solution from Example 7 or the UVC virus inactivated sample from Example 8 to final concentrations of 0.3% and 1%, respectively. The mixture was incubated with gentle stirring for at least 8 hours at 25°±2° C. The following examples were then conducted in a virus free manner in a virus free processing area.

EXAMPLE 9

Purification of Thrombin

The SD treated solution was diluted 1:1 with 20 mM Tris and pH adjusted to 7.0±1. The diluted, pH adjusted post-SD treated solution was chromatographed on a DEAE column (TOYOPEARL 650M resin) which was equilibrated with Buffer B. The pass-through and the following column rinse with Buffer B was collected and pooled. Prothrombin (unactivated prothrombin) and other DEAE bound proteins remained bound to the column while the activated prothrombin passed through the column effluent. The pH of the combined DEAE pass-through and rinse was adjusted to 8.0 with 1M, pH 10.0 Tris solution.

The pH adjusted DEAE pass-through was loaded onto a SP-SEPHAROSE column (Pharmacia) (400 gm SP-SEPHAROSE per liter of SP-Sepharose Equilibration Buffer (20 mM Tris [hydroxymethyl] aminomethane and 125 mM sodium chloride, pH 8.0)). After loading, the column was rinsed with Buffer E (20 mM Tris [hydroxymethyl] aminomethane and 150 mM sodium chloride, pH 8.0) and eluted with Buffer F (20 mM Tris [hydroxymethyl] aminomethane and 300 mM sodium chloride, pH 8.0). The column flow was monitored with a UV absorbance detector and the UV absorbance peak was collected.

EXAMPLE 10

15 Nanometer Filtration Virus Removal

The SP-SEPHAROSE Eluate solution was filtered through a 0.22 micron filter which was washed with 4.0 kg/ft$^2$ SP-SEPHAROSE Elution Buffer. The 0.22 micron filter SP-SEPHAROSE eluate solution was then filtered through a 15 nm hollow fiber ultrafiltration filter (Asahi PLANOVA 15 N, Japan), and washed both upstream and downstream with 1.2 kg SP-SEPHAROSE Elution Buffer.

EXAMPLE 11

Effect of 15 Nanometer Filtration on Virus Removal

The effect of the 15 nanometer filter on removal of the following viruses were examined: HAV (27–32 nm), encephalomyocarditis virus (EMC, 30–39 nm), porcine Parvo B19 (18–26 nm), sindbis (50–70 nm) and vesicular stomatitis virus (VSV, about 80 nm). 5 ml of each of HAV, EMC and Parvo B19 were added to three 400 ml samples of the thrombin concentrate purified as described in Example 9 at a protein concentration of 0.6 mg/ml. 5 ml of each of VSV and Sindbis were added to two 200 ml samples of thrombin concentrate at a protein concentration of 1.2 mg/ml. The virus added solutions were then prefiltered with a 0.22 μm filters before pumping them through 0.01 m$^2$ Planova 15 N filters, maintaining pressure at 10 psi, and filtrate flow rate as 3.5–5.0 ml/min.

Filtrate collections were pooled at every 50 ml for virus titration and thrombin clot assays. Virus infectious units (TCID$_{50}$) were calculated by the Spearman Karber method. HAV and Parvo B19 titers were determined by radioimmunofocus assay. Virus titration results showed that all samples from four filters were virus negative (with the exception of the sample of 180th ml filtrate from VSV filtration which was 0.1 log 10 virus positive (probably due to contamination)). The amount of virus removed from each samples was as follows: HAV, >7.5 log10; EMC, >5.7 log10; Parvo B19, >5.5 log10; VSV, >6.5 log10; and Sindbis, >5.6 log10. Thrombin clotting activity in filtrate samples were consistently as high as it was in the corresponding starting thrombin/virus mixtures.

EXAMPLE 12

Final Formulation of Thrombin

The 15 nm filtered thrombin from Example 10 was adjusted to 20 or 200 NIH equivalent thrombin units/ml with the addition of up to 15 mM CaCl$_2$, up to 1.0% of polyethylene glycol 4600, up to 300 mM sodium chloride, and up to 40 mM tris [hydroxymethyl] aminomethane. The pH was then adjusted to 7.4. The formulation was then filtered through a sterile 0.2 micron filter (Sartorius, SARTOBRAN pH) into a sterile container.

All publications mentioned hereinabove are hereby incorporated by reference in their entirety.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention in the appended claims.

What is claimed is:

1. A method for activating prothrombin to thrombin in a prothrombin complex composition comprising at least prothrombin, Factors V, VII, IX, and X, and phospholipid comprising the steps of:

(a) cold-incubating said prothrombin complex composition with 2–15 mM of Ca$^{2+}$ ions at a pH of 6.5–8.0 and at a temperature of 2°–8° C. until Factor VII contained in said composition is activated; and then (b) incubating the cold-incubated composition at a pH of 6.5–8.0 and at a temperature of 10°–25° C. for a period of time sufficient to activate prothrombin contained in said composition to thrombin.

2. The method of claim 1, wherein the total concentration of prothrombin and Factors V, VII, IX, and X in said prothrombin complex composition is at least 3–10 mg/ml.

3. The method of claim 1, wherein the concentration of Ca$^{2+}$ ions in step (a) is 3–10 mM.

4. The method of claim 1, wherein the concentration of $Ca^{2+}$ ions in step (a) is 4–6 mM.

5. The method of claim 1, wherein the source of $Ca^{2+}$ ions is $CaCl_2$.

6. The method of claim 1, wherein the pH in steps (a) and (b) is 6.8–7.3.

7. The method of claim 1, wherein the pH in steps (a) and (b) is 6.9–7.1.

8. The method of claim 1, wherein the temperature in step (a) is 3°–6° C.

9. The method of claim 1, wherein the cold incubation in step (a) is performed for at least 8 hours.

10. The method of claim 1, wherein the cold incubation in step (a) is performed for 12–18 hours.

11. The method of claim 1, wherein the temperature in step (b) is 18°–23° C.

12. The method of claim 1, wherein the incubation in step (b) is performed for 48–120 hours.

13. The method of claim 1, wherein the incubation in step (b) is performed for about 72 hours.

14. A method for preparing a thrombin concentrate from a prothrombin complex composition comprising at least prothrombin, Factors V, VII, IX, and X, and phospholipid comprising the steps of:

(a) cold-incubating said prothrombin complex composition with 2–15 mM of $Ca^{2+}$ ions at a pH of 6.5–8.0 and at a temperature of 2°–8° C. until Factor VII contained in said composition is activated; and then (b) incubating the cold-incubated composition at a pH of 6.5–8.0 and at a temperature of 10°–25° 0 C. for a period of time sufficient to activate prothrombin contained in said composition to thrombin; and (c) subjecting the composition containing thrombin to ion exchange chromatography to obtain the thrombin concentrate.

15. The method of claim 14, wherein the total concentration of prothrombin and Factors V, VII, IX, and X in said prothrombin complex composition is at least 3 mg/ml.

16. The method of claim 14, wherein the concentration of $Ca^{2+}$ ions in step (a) is 3–10 mM.

17. The method of claim 14, wherein the concentration of $Ca^{2+}$ ions in step (a) is 4–6 mM.

18. The method of claim 14, wherein the source of $Ca^{2+}$ ions is $CaCl_2$.

19. The method of claim 14, wherein the pH in steps (a) and (b) is 6.8–7.3.

20. The method of claim 14, wherein the pH in steps (a) and (b) is 6.9–7.1.

21. The method of claim 14, wherein the temperature in step (a) is 3°–6° C.

22. The method of claim 14, wherein the cold incubation in step (a) is performed for at least 8 hours.

23. The method of claim 14, wherein the cold incubation in step (a) is performed for 12–18 hours.

24. The method of claim 14, wherein the temperature in step (b) is 18°–23° C.

25. The method of claim 14, wherein the incubation in step (b) is performed for 48–120 hours.

26. The method of claim 14, which further comprises:

(b1) subjecting the composition containing thrombin to at least one viral inactivation treatment.

27. The method of claim 26, wherein said viral inactivation treatment comprises treating said composition with a solvent-detergent.

28. The method of claim 27, wherein said solvent-detergent is tri-n-butyl phosphate and TWEEN 80.

29. The method of claim 26, wherein said viral inactivation treatment comprises treating said composition with UV light.

30. The method of claim 26, wherein said viral inactivation treatment comprises treating said composition with UV light and a solvent-detergent.

31. The method of claim 30, wherein said solvent-detergent is tri-n-butyl phosphate and TWEEN 80.

32. The method of claim 14, wherein in step (c), the ion exchange chromatography comprises:

(1) applying the composition containing thrombin to a DEAE column equilibrated with an equilibration buffer containing 20 mM tris hydroxymethyl aminomethane and 125 mM sodium chloride, pH 7.0, and collecting the resulting material passed through said column;

(2) rinsing said column with a rinse buffer containing 20 mM tris hydroxymethyl aminomethane and 125 mM sodium chloride, pH 7.0, and collecting the resulting material passed through said column; and (3) combining said resulting materials from steps (1) and (2).

33. The method of claim 32, which further comprises:

(4) applying the combined resulting materials from step (3) to an SP-SEPHAROSE column equilibrated with an equilibration buffer containing 20 mM tris hydroxymethyl aminomethane and 125 mM sodium chloride, pH 8.0;

(5) rinsing said column with a rinse buffer containing 20mM tris hydroxymethyl aminomethane and 150 mM sodium chloride, pH 8.0; and (6) eluting the thrombin concentrate with an elution buffer containing 20 mM tris hydroxymethyl aminomethane and 300 mM sodium chloride, pH 8.0.

34. The method of claim 14, which further comprises:

(d) filtering the composition containing the thrombin concentrate through a 15 nm filter.

* * * * *